United States Patent [19]

Stock

[11] 4,077,679
[45] Mar. 7, 1978

[54] ROTARY DRUM FOR ROTARY AUTOCLAVE

[75] Inventor: Hermann Stock, Neumunster, Germany

[73] Assignee: Hermann Stock, Neumunster, Germany

[21] Appl. No.: 701,970

[22] Filed: Jul. 1, 1976

[30] Foreign Application Priority Data
Jul. 10, 1975 Germany .......................... 7521855[U]

[51] Int. Cl.² ............................................. F16C 19/00
[52] U.S. Cl. ........................................ 308/8; 308/36
[58] Field of Search ................. 308/6, 8, 27, 36, 37

[56] References Cited

U.S. PATENT DOCUMENTS

| | | | |
|---|---|---|---|
| 3,145,065 | 8/1964 | Cator | 308/6 R |
| 3,563,617 | 2/1971 | Pritchard | 308/6 R |

Primary Examiner—Richard A. Bertsch
Attorney, Agent, or Firm—Toren, McGeady and Stanger

[57] ABSTRACT

A plurality of parallel elongated side members are angularly spaced apart on an imaginary cylindrical surface and have first and second ends each. A first end-connecting assembly connects the first ends of the side members. A shaft-coupling sleeve is provided on the first end-connecting means and concentric with the cylindrical surface. At least one integral bearing race surrounds the side members and is axially spaced from said first end-connecting means. A second connecting assembly detachably connect the bearing race to the side members.

16 Claims, 3 Drawing Figures

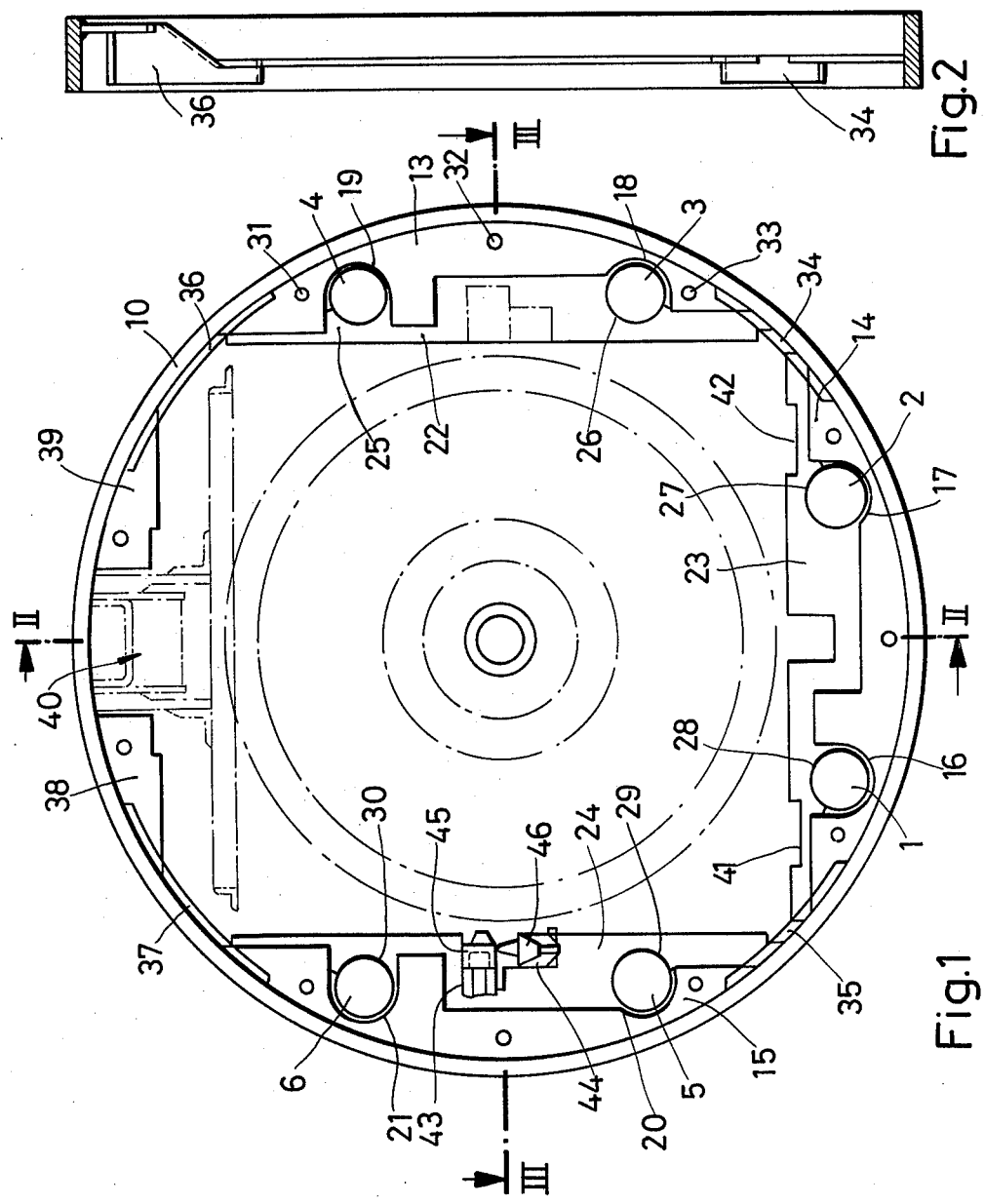

ROTARY DRUM FOR ROTARY AUTOCLAVE

SUMMARY OF THE INVENTION

This invention relates to a rotary drum for rotary autoclaves, comprising elongated side members extending in the longitudinal direction of the rotary drum and in which the side members are fixed.

Such rotary drums are of considerable size. They can receive baskets which contain the material to be sterilized, e.g., cans, and which are of considerable weight.

One end of such rotary drum is connected to a shaft, which extends out of the autoclave and is connected to drive means for rotating the rotary drum. At least the other end of the rotary drum is surrounded by a bearing race, the lower portion of which is in rolling contact with and supported by bearing rollers held in the housing of the autoclave.

The considerable stresses exerted on the bearing race by the rotating drum results in wear of the bearing race. This wear may amount to about 7 mm per year and results in high stresses on the other bearings, particularly those which support the shaft near the other end of the rotary drum. The at least one bearing race must be replaced from time to time.

In known rotary drums, the suitably tubular, elongated side members are fitted in openings, which are confined throughout their circumference and formed in webs that are secured to the bearing races. The tubular side members are welded to the webs at the openings.

The replacement of the bearing races of these rotary drums involves a considerable expenditure. Elements of construction must be cut open for this purpose and even the tubular spars are damaged in many cases. The entire rotary drum must be removed, and it has previously been necessary to weld a reinforcing ring to the drum and subsequently to surface-grind said ring. This requires also a sufficiently large lathe.

Known rotary drums are provided with guide rails, which are connected to the webs and serve to guide and support the baskets and may be provided with rollers.

It is an object of the invention to facilitate the replacement of the at least one bearing race and particularly to enable a replacement without need for a cutting of parts.

This object is accomplished according to the invention in that the side members are detachably secured to the bearing race. As a result, the at least one bearing race can be withdrawn from the side members in an endwise direction. According to a further feature of the invention the rotary drum is held together by the bearing race assembly even though the side members are detachably secured to the at least one bearing race. This feature greatly facilitates the replacement of the bearing race and enables such replacement to be carried out in a relatively simple manner on the site of the machine. Damage to the rotary drum itself by the replacement is precluded.

A detachable fixation can be accomplished in various ways. For instance, the above-mentioned webs may be provided with apertures, and flanged bushings disposed on both sides of the apertures may be detachably secured to the side members, e.g., by radial screws.

In accordance with a particularly preferred feature, circumferentially spaced apart lugs are permanently secured to the bearing race and formed with inwardly open apertures for receiving the side members and with additional profiled portions for engagement with connecting means, and straps are provided, which are formed with complementary apertures conforming to the cross-section of the side members and are adapted to be connected to the lugs. In this arrangement, each web consists of two parts and includes an inner part, which is described as a strap and detachably connected to an outer web part, which has an aperture that corresponds virtually to one-half of the previous apertures.

The lugs may also be formed with apertures which conform to the cross-sections of the side members.

The side members are preferably welded to the straps at the apertures thereof. In that case the side members are firmly connected at least in pairs also adjacent to the replaceable bearing race. According to a further feature, the straps are internally connected to form a substantially U-shaped component. A preferred embodiment comprises a plurality of weblike lugs.

If the side members are welded to the straps, the apertures in the lugs are preferably oversize relative to the side members so that the subassembly which comprises the side members can be used without need for close tolerances regarding the locations of the lugs at the bearing race. Above all, the lugs and straps can be assembled in close contact with each other regardless of the seam welds provided adjacent thereto.

It will be understood that the lugs are designed for a sufficiently large overlap with the straps. In a preferred arrangement, the oversize aperture which receives one of the two side members that are held together by a strap is U-shaped and has a depth which is substantially as large as the diameter or largest cross-sectional dimension of a side member.

Various kinds of connecting members may be provided. The lugs and straps are preferably interconnected by threaded fasteners. The resulting assembly is virtually integral in the radially outward direction as far as the side members are concerned. This is particularly desirable as regards the stresses exerted during the rotation of the drum. On the other hand, a detachable fixation is provided at the inwardly open apertures of the lugs.

Each lug and each strap preferably engages two side members. This results in a highly economical structure.

Although a plurality of bearing races may be provided, a preferred arrangement comprises only one bearing race, which is provided at that end of the drum which is remote from the shaft which supports the rotary drum, i.e., virtually at the charging end of the drum. Such supporting arrangement may be used with the stable rotary drum, which comprises elongated side members consisting suitably of tubes.

According to a preferred feature, guide rails and/or rollers, known per se, which serve to guide and support baskets, are mounted on the straps. In such an arrangement, such rails and/or rollers when damaged can also be replaced more easily than before because they are mounted on detachable elements consisting of the straps.

The invention will now be described with reference to an illustrative embodiment, which is shown on the drawing, in which:

FIG. 1 is an end view showing a rotary drum which embodies the invention,

FIG. 2 is a fragmentary sectional view taken on line II—II in FIG. 1 and showing only the bearing race.

In all Figures, like parts are designated with the same reference characters.

Figure 3:
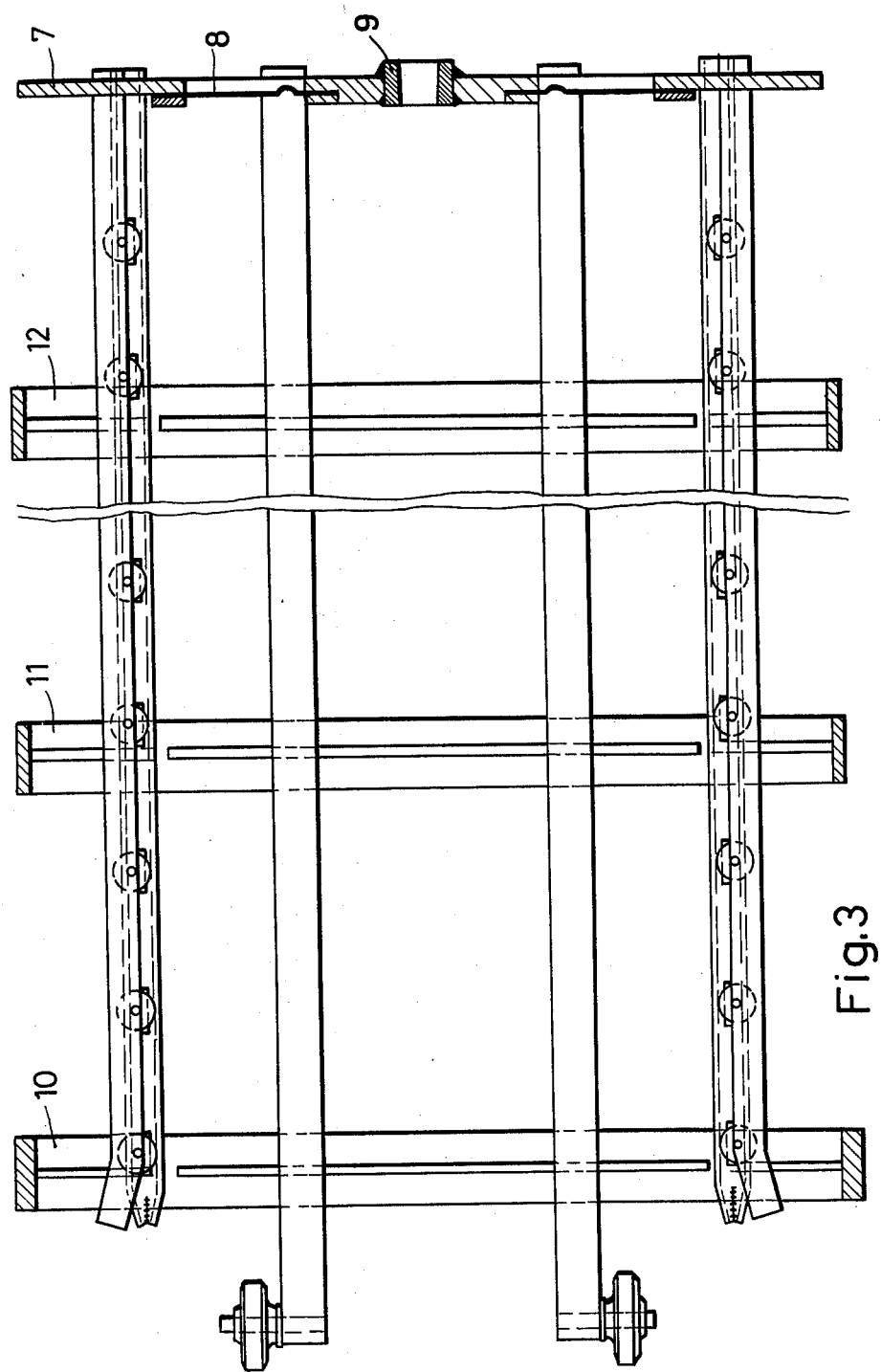
FIG. 3 is a sectional view taken on line III—III in FIG. 1.

The rotary drum comprises six side members 1 to 6, which extend throughout the length of the drum and are secured at one end in a circular plate 7, which has in its intermediate portion a coupling sleeve 9, which is connected to the plate 7 by a universal joint or sheet metal arms 8 and in which a rotatable drive shaft, not shown, is mounted. The tubular side members are disposed on a circle that is centered on the center line of the rotary drum and a bearing race. That center line is aligned with the center line of the drive shaft. At their other end, the side members 1 to 6 are carried by a bearing race 10. Between their ends, the side members may be held together by additional confining rings 11, 12, to which the side members may be secured by means which are similar to the means connecting the side members to the bearing race 10. The confining rings 11, 12 have external dimensions which are undersize relative to those of the bearing race 10.

The bearing race 10 is provided with, e.g., three retaining lugs 13, 14, 15, which are circumferentially spaced apart and formed in their inner edge with inwardly open apertures 16 to 21 for receiving the side members. These apertures 16 to 21 are oversize relative to the side members 1 to 6. For instance, their radius is larger by about 8 mm. One aperture 21, 16, 19 of each pair thereof is smaller in depth toward the center than the diameter of a side member. The side members 1 to 6 protrude into these apertures 16 to 21.

Straps 22 to 24 are associated with respective ones of the webs 13 to 15 and are formed with externally open apertures 25 to 30, which conform to the cross-section of the side members 1 to 6. Particularly if the apertures 16 to 21 are oversize, the side members are welded to the straps 22 to 24 at these apertures 25 to 30. All apertures may conform to the cross-section of the side members so that these are located on the lugs during the assembly, e.g., the fixation of the straps.

The embodiment described hereinbefore is preferred. It is apparent that the inner edge of each lug extends substantially parallel to the adjacent straps and is formed with stepped sections.

These straps and lugs are provided with holes which receive bolts 31 to 33 for connecting the straps to the lugs.

Reinforcing lugs 34, 35 are secured, e.g., by welding to the inside of the bearing race between the retaining lugs, which extend at right angles to the rolling contact surface of the bearing race. The reinforcing lugs overlap adjacent ends of the retaining lugs and embrace the same so as to improve the stability of the assembly.

Such reinforcing lugs 36, 37 are also shown in the upper portion of FIGS. 1 and 2 and provided between the upper ends of the side members 13, 15 and guide lugs 38, 39, which are welded to the inside peripheral surface of the bearing and serve to guide a clamp 40, which is diagrammatically shown and serves to retain baskets that have been introduced.

Profiled elements 41, 42 and particularly guide rails 43, 44 provided with rollers 45, 46 for guiding and supporting baskets are provided on the detachably secured straps 22 to 24 so that these parts when damaged may also be replaced individually and without need for completely diassembling the rotary drum.

The lugs 13 to 15 and the reinforcing lugs 34 to 37 are suitably welded to the bearing race.

The rollers 45, 46 are rotatable on axles which extend at right angles to each other and are mounted on the lugs 22 to 24. FIG. 3 shows the rows of rollers in the corresponding section plane.

It is pointed out that the confining rings 11, 12 are detachably secured by connecting means which are similar to the connecting means 13, 15, 22, 24 shown for the bearing race 10 and embody the same features and that connecting means such as are shown in FIG. 1 are provided also adjacent to the additional confining rings 11, 12.

What is claimed is:

1. A rotary drum for use in a rotary autoclave, comprising
a plurality of parallel axially elongated side members which are angularly spaced apart around and extend along an imaginary cylindrical surface in parallel relation with the axis thereof, and each having a first and a second end spaced apart in the axial direction of the imaginary cylindrical surface,
end-connecting means extending transversely of the axial direction of the imaginary cylindrical surface connecting said first ends of said side members,
shaft-coupling means provided on said end-connecting means and concentric with the axis of said imaginary cylindrical surface,
at least one integral bearing race surrounding said side members and spaced apart from said first end-connecting means in the axial direction of the imaginary cylindrical surface, and
second connecting means detachably connecting said bearing race to said side members.

2. A rotary drum as set forth in claim 1, in which said second connecting means comprise
lug means which are secured to said bearing race and formed with angularly spaced, radially inwardly open first apertures which receive said side members,
straps formed with second apertures which conform to the cross-section of said side members, and
fastening means detachably connecting said straps to said lug means in a position in which said second apertures adjoin respective ones of said first apertures.

3. A rotary drum as set forth in claim 2, in which said side members are welded to said straps at said second apertures.

4. A rotary drum as set forth in claim 2, in which said first apertures are oversize with respect to the cross-section of said side members.

5. A rotary drum as set forth in claim 2, in which said second connecting means comprise threaded fasteners detachably connecting said lug means to said straps.

6. A rotary drum as set forth in claim 2, in which:
said lug means comprise a plurality of retaining lugs, each of which is formed with two of said first apertures and
each of said straps is connected to one of said retaining lugs and formed with two of said second apertures.

7. A rotary drum as set forth in claim 6, in which:
one of said first apertures of each of said lugs is U-shaped and has a depth which is substantially as large as the largest cross-sectional dimension of the side member received thereby.

8. A rotary drum as set forth in claim 2, in which said lug means comprise profiled portions engaged by said fastening means.

9. A rotary drum as set forth in claim 2, in which each of said second apertures has a configuration which substantially corresponds to one-half of the cross-section of a side member.

10. A rotary drum as set forth in claim 2, which is adapted to receive baskets containing material to be treated in said autoclave and in which:
said straps support guide rails which are adapted to guide and support said baskets.

11. A rotary drum as set forth in claim 10, in which rollers are rotatably mounted in said guide rails and engageable with said baskets.

12. A rotary drum as set forth in claim 11, in which each of said second apertures has the configuration of a semicircle.

13. A rotary drum as set forth in claim 1, in which:
said side members are tubular and
each of said second apertures has the configuration of a segment of a circle.

14. A rotary drum as set forth in claim 1, in which:
said bearing race has an inside peripheral surface,
said lug means comprise a plurality of angularly spaced retaining lugs, which protrude from said inside peripheral surface,
reinforcing lugs are secured to said inside peripheral surface between adjacent ones of said retaining lugs and overlap said adjacent retaining lugs
guide lugs are welded to said bearing race adjacent to certain ones of said retaining lugs,
additional reinforcing lugs are provided on said bearing race and overlap said guide lugs and said retaining lugs adjacent thereto, and
clamping means are provided, which are guided by said guide lugs.

15. A rotary drum as set forth in claim 1, in which said bearing race is connected by said second connecting means to said side members at said second end thereof.

16. A rotary drum as set forth in claim 1, in which
at least one confining ring which is smaller in outside diameter than said bearing race surrounds said side members between said first end-connecting means and said bearing race and
additional connecting means are provided, which detachably connect said confining ring to said side members.

* * * * *